(12) United States Patent
Arakaki et al.

(10) Patent No.: US 6,773,913 B2
(45) Date of Patent: Aug. 10, 2004

(54) DEVICE AND PROCESS FOR PURIFYING VECTORS

(75) Inventors: Sakae Arakaki, Yagibaru Terrace Y-10, 793, Aza Yagibaru, Kitanakagusuku-son, Nakagami-gun, Okinawa (JP); Masaru Nagamine, 108-9, Shuri Sueyoshi-cho 1-chome, Naha-shi, Okinawa (JP); Masanao Kikukawa, 24-10, Minatogawa 1-chome, Urasoe-shi, Okinawa (JP)

(73) Assignees: Sakae Arakaki (JP); Masaru Nagamine (JP); Masanao Kikukawa (JP); Advanced Medical Biological Science Institute Co., Ltd. (JP)

(*) Notice: Subject to any disclaimer, the term of this patent is extended or adjusted under 35 U.S.C. 154(b) by 77 days.

(21) Appl. No.: 09/964,377

(22) Filed: Sep. 28, 2001

(65) Prior Publication Data

US 2002/0127704 A1 Sep. 12, 2002

(30) Foreign Application Priority Data

Mar. 6, 2001 (JP) ........................................ 2001-062404

(51) Int. Cl.$^7$ .............................................. C12M 1/12
(52) U.S. Cl. ................................ 435/297.1; 435/306.1; 435/308.1; 435/320.1; 536/25.4
(58) Field of Search ...................... 536/25.4; 435/320.1, 435/297.1, 306.1, 308.1

(56) References Cited

U.S. PATENT DOCUMENTS

| | | | |
|---|---|---|---|
| 6,313,285 B1 | * | 11/2001 | Butler et al. |
| 6,455,298 B1 | * | 9/2002 | Groner et al. |
| 2002/0034735 A1 | * | 3/2002 | Carrion et al. |

FOREIGN PATENT DOCUMENTS

| | | |
|---|---|---|
| JP | 5-31332 | 2/1993 |
| JP | 2001-513419 | 9/2001 |
| WO | WO 99/07458 | 2/1999 |

OTHER PUBLICATIONS

Yodo–sha, "Separate Volume of Experimental Medicine, Genetic Engineering Handbook," Mar. 20, 1991, pp 18–25.
Purification of Plasmid DNA by Tangential Flow Filtration by Kahn et al., Biotechnology and Bioengineering, vol. 69, No. 1, Jul. 5, 2000, pp. 102–106.

Removal of Bacterial Endotoxin from Recombinant Plasmid DNA by Phase Separation, Pharmaceutical Research, 1997, vol. 14, No. 11, pp. 351–352.

Simple and rapid preparation of plasmid template by a filtraion method using microtiter filter plates by Itoh et al., Nucleic Acids Research, 1997, vol. 25, No. 6, pp. 1315–1316.

A Filtration Method for Plasmid Isolation Using Microtiter Filter Plates, Ruppert et al., Analytical Biochemistry, 1995, vol. 230, No. 1, pp. 130–134.

The processing of a plasmid–based gene from E. Coli Primary recovery by filtration, I. Theodossiou et al., Bioprocess Engineering 16, 1997, pp. 175–183.

Short Technical Reports, Effects of Iipopolysaccharide on Transfection Efficiency in Eukaryotic Cells, BioTechniques, vol. 19, No. 6, 1995, pp. 932–940.

Research Report, Reexamination of the Effect of Endotoxin on Cell Proliferation and Transfection Efficiency, Butash et al., BioTechniques, vol. 29, No. 3, 2000, pp. 610–619.

* cited by examiner

Primary Examiner—James Ketter
(74) Attorney, Agent, or Firm—Parkhurst & Wendel, L.L.P.

(57) ABSTRACT

In a vector purification device, bacteria containing vectors are cultured in a culture medium in a culture tank, the culture medium is concentrated by filtration with a first TFF film, and the concentrated culture medium is replaced with a buffer solution by filtering a mixture of the culture medium and the buffer solution by the TFF film while supplying the buffer solution from a buffer tank. The bacteria subjected to bacteriolysis by an alkali solution supplied from an alkali tank are passed through a second TFF film to remove undesired substances. Since the TFF films are used in place of a centrifugal separator for concentration or the like, a series of operations can be carried out continuously in a closed system. Further, a crudely purified vector solution is treated with a surfactant to separate vector DNAs from endotoxins as separate layers, and the endotoxins are removed. According to the device, a series of operations such as concentration of the culture medium can be carried out continuously in a closed system, and high-purity vectors can be obtained.

2 Claims, 3 Drawing Sheets

FILTRATE

DEVICE AND PROCESS FOR PURIFYING VECTORS

BACKGROUND OF THE INVENTION (i) Field of the Invention

The present invention relates to a device and a process for purifying vectors, and more particularly, it relates to a device and a process for concentrating a solution containing hosts and/or vectors, replacing the solution with another solution, or removing undesired substances from the solution.

(ii) Description of the Related Art

Along with a rapid development in a genetic engineering industry in recent years, a need for manipulating high-purity vectors on a large scale has been increasing. However, it takes a long time to obtain a large amount of the high-quality vectors, since a complex device must be used to purify them. In addition, the operation of the device is also complicated and requires some technical experience.

In particular, a centrifugal separator has heretofore been used to concentrate a solution in which hosts containing vectors are cultured in a purification process of vectors. Therefore, there exist problems that this culture medium cannot be concentrated in a closed system and that it is difficult to achieve the scale-up of the concentration. For example, "Separate volume of Experimental Medicine, Genetic Engineering Handbook" (issued on Mar. 20, 1991 by Yodo-sha) describes "Mass preparation of vector DNA", which is carried out by the repetition of centrifugation, on the pages 21 to 23. Furthermore, also in order to remove undesired substances such as small proteins and small DNAs contained in vector DNAs, a centrifugal separator has heretofore been used, and hence the similar problems have been present. In addition, endotoxins cannot be removed by a centrifugal separator or an ion exchange column, and must be removed by a special column such as a hydrophobic column.

Therefore, a device or a process has been desired which can concentrate a solution containing hosts and/or vectors, replace the solution with another solution or remove undesired substances from the solution in a closed system. Further, a device or a process has been desired which can remove endotoxins effectively. Further, a device or a process by which a large amount of high-quality vectors can be easily obtained in a closed system have been desired.

Meanwhile, a filtration film for TFF (Tangential Flow Filtration) (referred to as "TFF film" hereinafter) has been known as a type of filtration films. However, the use of the TFF film for concentrating a solution containing hosts and/or vectors or removing undesired substances from the solution has not been known in the field of genetic engineering.

SUMMARY OF THE INVENTION

It is therefore an object of the present invention to provide a device or a process which can concentrate a solution containing hosts and/or vectors, replace the solution with another solution and remove undesired substances from the solution in a closed system.

Further, it is an object of the present invention to provide a device or a process by which endotoxins can be effectively removed.

Further, it is an object of the present invention to provide a device or a process by which a large amount of high-quality vectors can be easily obtained in a closed system.

The present inventors have made intensive studies and completed the present invention by finding that the use of a TFF film or a surfactant facilitates the concentration of the solution containing hosts and/or vectors, replacement of the solution with another solution or removal of undesired substances from the solution. In addition, it has been found that the vectors purified by the present invention are of high purity. In particular, the present invention effectively utilizes a TFF film, which has never been used for gene manipulation before, for gene manipulation for the first time.

According to a first aspect of the present invention, a concentrating device is provided that comprises a TFF film which filtrates a solution containing hosts and/or vectors to concentrate the solution.

According to a second aspect of the present invention, a replacing device is provided that comprises a TFF film which filtrates a mixture of a first solution containing hosts and/or vectors and a second solution while supplying the second solution to replace the first solution with the second solution.

According to a third aspect of the present invention, an undesired substance removing device is provided that comprises a TFF film which removes undesired substances from a solution containing hosts and/or vectors.

According to a fourth aspect of the present invention, an endotoxin removing device is provided that comprises a surfactant supply unit which supplies a surfactant, a mixing vessel in which a crudely purified vector solution containing endotoxins is mixed with a surfactant to separate the solution into a water layer which mainly contains vector DNAs and a surfactant layer which contains the endotoxins, and a discharge unit which discharges the surfactant layer.

According to a fifth aspect of the present invention, a concentrating process is provided that comprises the step of filtering a solution containing hosts and/or vectors by using a TFF film.

According to a sixth aspect of the present invention, a replacing process is provided that comprises the step of filtering a mixture of a first solution containing hosts and/or vectors and a second solution by using a TFF film, while supplying the second solution, to replace the first solution with the second solution.

According to a seventh aspect of the present invention, an undesired substance removing process is provided that comprises the step of removing undesired substances from a solution containing hosts and/or vectors by using a TFF film.

According to an eighth aspect of the present invention, a process for removing endotoxins is provided that comprises the steps of mixing a crudely purified vector solution containing endotoxins with a surfactant, separating the solution into a water layer which mainly contains vector DNAs and a surfactant layer which contains the endotoxins and discharging the surfactant layer.

The TFF film used in the present invention is a type of filtration films and has a number of pores. The TFF filtration using this film is also called "cross-flow filtration". Its mechanism is shown in FIG. 3. As shown in FIG. 3, as a solution flows parallel to the surface of the film (from left to right in the direction indicated by the arrow A in FIG. 3), a portion of the solution which may contain specific substances passes through pores (or is filtered) (downward in the direction indicated by the arrow B in FIG. 3). The sizes of substances which pass through or do not pass through the pores depend on the sizes of the pores. In the present invention, the sizes can be appropriately determined according to application purposes. In general, the direction in which the solution flows is perpendicular to the direction in which the substances pass through the pores. In the case of the present invention, however, the angle between the two directions is not limited to a right angle.

Further, hosts used in the present invention are not particularly limited. Illustrative examples of the hosts include bacteria such as *Escherichia coli, Bacillus subtilis* and yeast which are generally and frequently used in genetic engineering.

Further, vectors used in the present invention are not particularly limited. Illustrative examples of the vectors include plasmids, phages and cosmids which are generally and frequently used in genetic engineering.

The concentrating device and process according to the present invention can be used, for example, for concentrating a culture medium which contains hosts containing vectors and various treatment solutions used in vector purification processes. Further, they can also be used for concentrating a solution which contains hosts containing target endogenous substances.

Further, in the replacing device and process of the present invention, a first solution can be replaced with a desired second solution. That is, by filtering a mixture of the first solution and the second solution by a TFF film while supplying the second solution to the first solution, the first solution is replaced by the second solution. The replacing device and process can be used, for example, for replacing the solution with a buffer solution. This replacing procedure can be carried out subsequently to or concurrently with the above concentrating procedure.

In the purification of vectors, it is difficult to extract vectors from hosts remaining in a culture medium. Therefore, the culture medium must be generally replaced with a neutral buffer solution. By using the concentrating and replacing devices and processes of the present invention, the replacement of the culture medium with a buffer solution can be carried out continuously after the concentration of the culture medium.

The undesired substance removing device and process according to the present invention can be used, for example, for removing undesired substances such as small proteins, small DNAs and endotoxins, e.g., debris, host-derived proteins, RNA and chromosome DNA fragments. This undesired substance removing procedure can be carried out subsequently to or concurrently with the above replacing or concentrating procedure.

In the conventional process of purifying vectors, endotoxins have been unable to be removed even by using a centrifugal separator or an ion exchange column and have had to be removed by using a special column such as a hydrophobic column. However, by using a TFF film, endotoxins can be removed from a crudely purified vector solution without using the special column. In order to dissociate the endotoxins from the vectors, the crudely purified vector solution can be treated with a surfactant such as a nonionic surfactant.

A surfactant used in the endotoxin removing device and process according to the present invention is mixed with the crudely purified vector solution to be separated into a water layer and a surfactant layer. Primarily, vector DNAs are contained in the water layer and endotoxins are contained in the surfactant layer. By removing the surfactant layer, the endotoxins can be removed.

For example, a surfactant used in the present invention may be a surfactant which is mixed with the crudely purified vector solution to form into a single layer at low temperatures and is separated into a water layer and a surfactant layer at high temperatures.

An example of such a surfactant is a nonionic surfactant which is separated into two layers by temperature control, as exemplified by Triton (registered trademark) X114. In the case of Triton X114, it is mixed with a crudely purified solution to form into a single layer at about 4° C. and separated into two layers at about 60° C.

As described above, according to the concentrating, replacing and undesired substance removing devices and processes of the present invention, the concentration of a solution containing hosts and/or vectors, replacement of the solution with another solution and removal of undesired substances from the solution can be carried out easily in a closed system. In addition, the scale of the purification system can be changed easily.

According to the endotoxin removing device and process of the present invention, endotoxins can be removed effectively.

When the above devices and processes of the present invention are combined to purify vectors, a large amount of high-purity vectors can be obtained by continuous procedures in a closed system.

BEST MODE OF CARRYING OUT THE INVENTION

A description will be given to one embodiment of the present invention hereinafter. However, the scope of the present invention shall not be limited to this embodiment.

Figure 1:
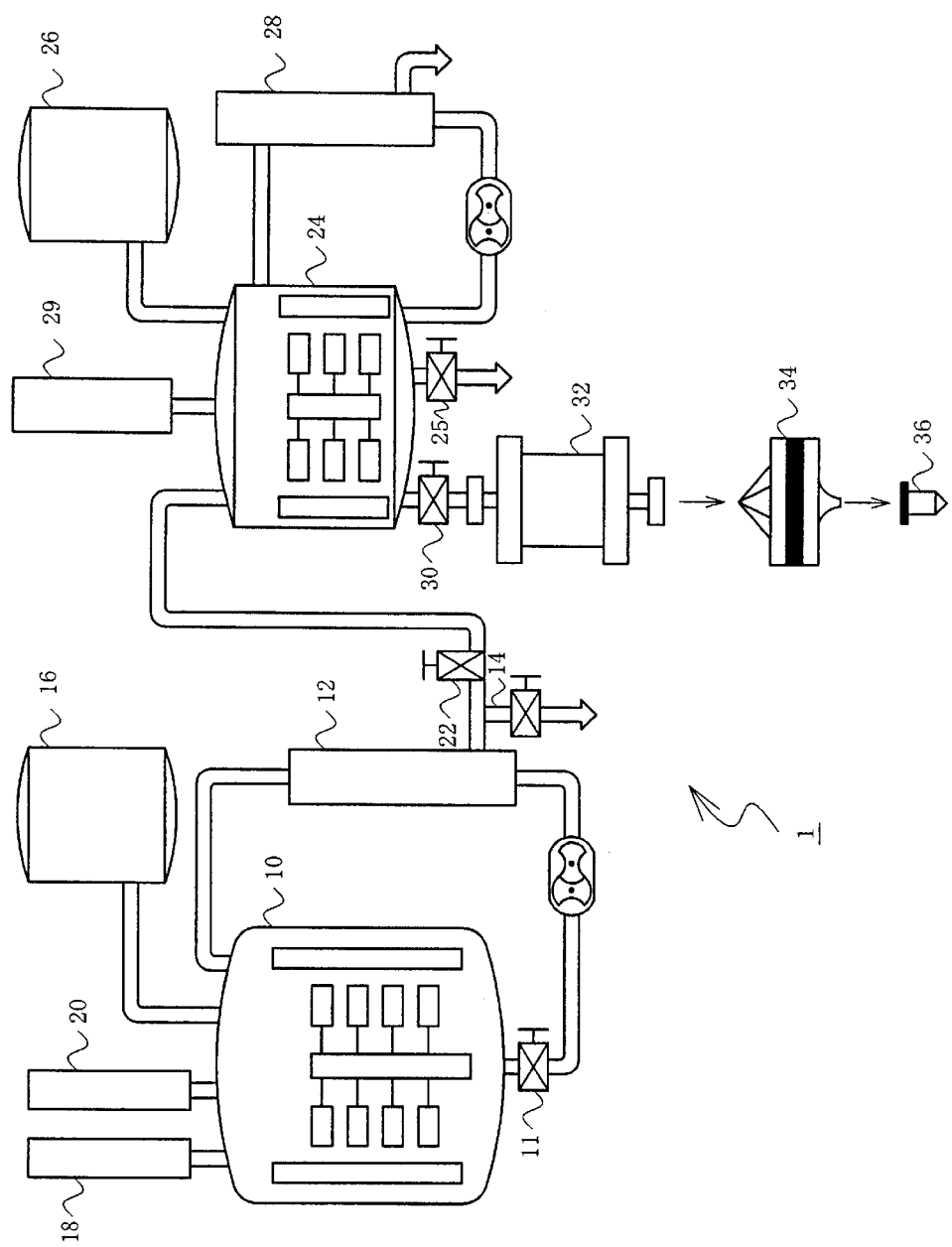
FIG. 1 is a diagram showing a plasmid purification device according to an embodiment of the present invention.

FIG. 1 is a diagram showing a plasmid purification device according to the present invention. In FIG. 1, reference numeral 1 denotes a plasmid purification device which purifies plasmids from bacteria bodies; 10 a culture tank in which a culture medium is stored and bacteria are cultured in the culture medium; 12 a first TFF film (concentrating device, replacing device and undesired substance removing device) which concentrates a culture medium (first solution), replaces the first solution with a buffer solution (second solution) or removes undesired substances; 11, 14, 22, 25 and 30 valves for opening and closing flow paths; 16 a first buffer tank which supplies a buffer solution; 18 an alkali tank which supplies an alkali solution; 20 a neutralization tank which supplies a neutral solution; 24 a tank which stores a crudely purified plasmid solution; 26 a second buffer tank which supplies a buffer solution for a column; 28 a second TFF film (concentrating device, replacing device and undesired substance removing device) which removes undesired substances from a crudely purified solution (first solution), replaces the first solution with a buffer solution for a column (second solution) or concentrates the crudely purified solution; 29 a surfactant tank which supplies a surfactant; 32 an ion exchange column which purifies crudely purified plasmids; 34 a sterile filter which sterilizes purified plasmids; and 36 a bottle which stores the plasmids.

The above culture tank 10 is a tank equipped with devices for providing various conditions for growing hosts. The buffer solution used is not particularly limited and any buffer solutions suitable for the purification of the plasmids can be used.

Although the pore size of the first TFF film 12 is not limited to particular sizes, it is preferably not larger than about 2 $\mu$m, more preferably about 1 $\mu$m. Although the first TFF film 12 is not limited to particular types, it is preferably a hydrophilic TFF film with low protein adsorption and the pH range of 2 to 14.

Although the pore size of the second TFF film 28 is not limited to particular sizes, it is preferably in a range of about 10 nm to about 4 nm, more preferably about 5 nm. Although the second TFF film 28 is not limited to particular types, it is preferably a hydrophilic TFF film with low protein adsorption and no DNA adsorption.

Figure 2:
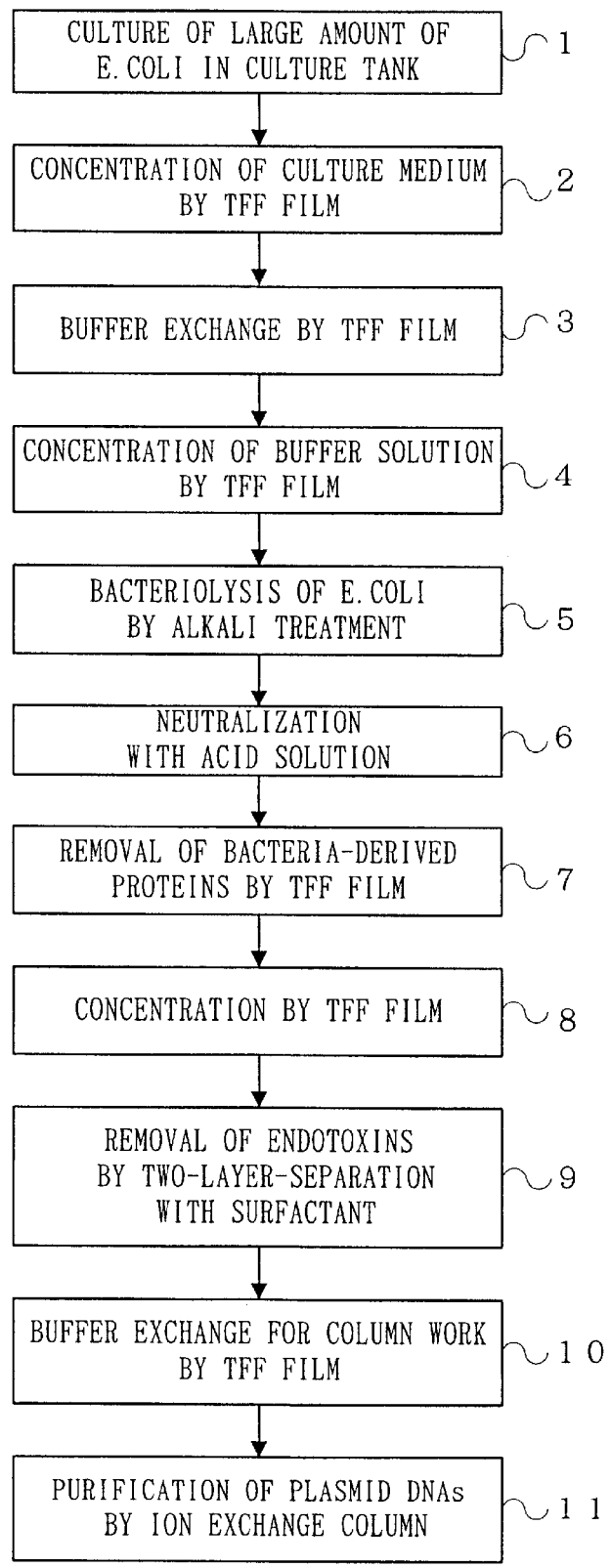
FIG. 2 is a flowchart showing a plasmid purification process according to an embodiment of the present invention.

Next, a description will be given to the operation of the plasmid purification device 1 with reference to the flowchart shown in FIG. 2.

Figure 3:
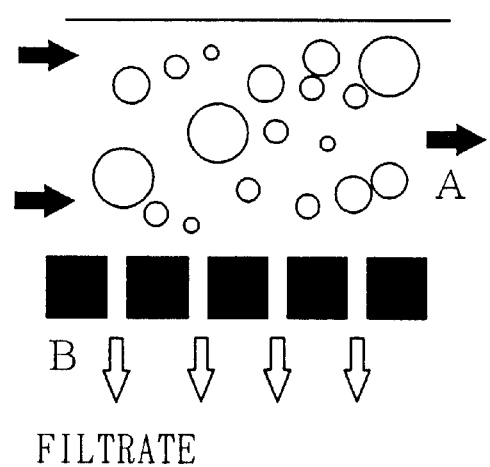
FIG. 3 is a schematic diagram showing the mechanism of a TFF film used in the present invention.

Firstly, a large amount of *Escherichia coli* are cultured in the culture tank 10 (Step 1). Then, the valve 11 is opened to allow a culture medium containing the bacteria bodies of *Escherichia coli* to pass through the first TFF film 12. FIG. 3 schematically shows the mechanism of the TFF film. In FIG. 3, the culture medium flows from left to right in the direction of the arrow A. The bacteria bodies in the culture medium do not pass through the TFF film 12, allowing only a portion of the culture medium to pass through the TFF film 12 downward in the direction of the arrow B. The portion of the culture medium which has passed through the TFF film 12 is discarded by opening the valve 14. In this way, the culture medium is concentrated by passing through the TFF film 12 (Step 2).

After the culture medium is concentrated by the above concentrating step, a buffer solution is supplied from the first buffer tank 16 to the culture tank 10. Then, a mixture of the buffer solution and the concentrated culture medium is passed through the TFF film 12. Referring again to FIG. 3, while the mixed solution flows in the direction of the arrow A, a portion of the mixed solution passes through the TFF film 12 in the direction of the arrow B. By passing the mixed solution through the TFF film 12 while supplying the buffer solution, the culture medium can be replaced by the buffer solution (Step 3). Further, the buffer solution is concentrated by using the TFF film 12 (Step 4).

Next, an alkali solution is supplied from the alkali solution tank 18 to the culture tank 10 to subject the bacteria bodies of *Escherichia coli* contained in the culture tank 10 to bacteriolysis (Step 5). As a bacteriolytic agent, liposome or the like may be used as well as the alkali solution. The alkali solution may contain SDS, Tween (registered trademark) 20, Tween 80, Triton (registered trademark) X-100, Triton X-114 and Nonidet (registered trademark) P40.

Next, an acid solution is supplied from the neutral solution tank 20 to the culture tank 10 to neutralize the target solution (Step 6). Further, the neutralized solution is passed through the TFF film 12 to remove debris, thereby obtaining a crudely purified plasmid solution.

Next, the valve 22 is opened to allow the crudely purified solution to flow into the tank 24. The crudely purified solution is passed from the tank 24 through the second TFF film 28. Referring again to FIG. 3, while the crudely purified solution flows in the direction of the arrow A, undesired substances such as small proteins, e.g., proteins derived from the bacteria bodies, and small DNAs pass through the second TFF film 28 in the direction of the arrow B. The filtrate containing the undesired substances is discarded. As a result, a crudely purified solution free from the undesired substances is obtained (Step 7).

Further, this crudely purified solution is concentrated by using the second TFF film 28 (Step 8).

Next, while the internal temperature of the tank 24 is maintained at about 4° C. by using a temperature controller (not shown), a nonionic surfactant is supplied from the surfactant tank 29 to the tank 24 and mixed with the crudely purified solution by agitation. Then, the internal temperature of the tank 24 is increased to about 60° C. by using the temperature controller to separate the mixed solution into an upper water layer containing plasmid DNAs and a lower layer containing endotoxins. The valve 25 is opened to discharge the lower surfactant layer from the bottom of the tank 24, thereby removing the endotoxins (Step 9). In this case, since the water layer and the surfactant layer have different light transmittances, by providing a sensor which senses light transmittance to the valve 25, the valve 25 can be opened and closed automatically according to changes in light transmittance of the waste solution.

Next, a buffer solution for column work is supplied from the second buffer tank 26 to the tank 24, and a mixture of the buffer solution and the crudely purified solution is passed through the second TFF film 28. Referring again to FIG. 3, while the mixed solution flows in the direction of the arrow A, a portion of the mixed solution passes through the TFF film 28 in the direction of the arrow B. By passing the mixed solution through the TFF film 28 while supplying the buffer solution for column work, the crudely purified solution is replaced with the buffer solution for column work (Step 10). Further, the buffer solution is concentrated as required.

Next, the valve 30 is opened to allow the crudely purified solution to flow into and pass through the ion exchange column 32, thereby purifying plasmid DNAs (Step 11).

Finally, the plasmid DNAs are passed through the sterile filter 34 and stored in the bottle 36.

In this plasmid purification device 1, the concentration of a culture medium, replacement of the culture medium with a buffer solution and purification of plasmid DNAs can be carried out continuously in a closed system in a short time by using the TFF films 12 and 28. Further, the purification of the plasmid DNAs can be scaled up or down with ease. In addition, since the TFF films 12 and 28 are smaller in size and less expensive than a centrifugal separator or the like, the size or cost of the whole device can be reduced.

Further, since a plurality of operations such as the concentration of a culture medium or a crudely purified solution, replacement thereof with a buffer solution and removal of undesired substances therefrom can be carried out by a single TFF film, the size or cost of the device can be further reduced.

Further, since a centrifugal separator which has been conventionally used for concentration of a culture medium or the like is not used, a series of operations can be carried out continuously in a completely closed system.

Next, the present invention will be described in more detail with reference to Examples.

EXAMPLE 1

Firstly, *Escherichia coli* containing plasmids (beta gal plasmid vectors) was cultured in a culture tank containing 10 liters of LB culture media one night (14 hours). Then, the culture medium containing the *Escherichia coli* bodies was passed through a TFF film (Prostac, Dulapora PVDF 0.1 $\mu$m, Millipore Co., Ltd.) to condense the solution to 1 liter.

Next, while 10 liters of a buffer solution (Tris-C125 mM, pH 8.0, EDTA 10 mM) (referred to as "TE" hereinafter) was supplied to the condensed culture medium, a mixture of theses solutions was passed through the TFF film (Prostac), thereby replacing the culture medium with the buffer solution. Further, the buffer solution was condensed to 1 liter by using the above TFF film (Prostac).

Next, 1 liters of a 200-mM NaOH solution (containing 1% of SDS) was added to the *Escherichia coli* body for bacteriolysis. Thereafter, 1 liter of 3.0-M potassium acetate (pH 5.5) was added to the above solution to neutralize the solution.

The neutralized solution was passed through the above TFF film (Prostac) to remove debris, thereby recovering 3 liters of filtrate.

The recovered filtrate was passed through a TFF film (Pericon 2 PLCHK (100 KD regenerated cellulose), Millipore Co., Ltd.) to remove low-molecular-weight proteins and the like and concentrated to 0.5 liters.

Next, the concentrated solution was supplied with 10 liters of a buffer solution (TE) containing 5% of a nonionic surfactant (Triton X-114) and agitated at about 4° C. Thereafter, the mixture was heated to about 60° C. and left to stand over 30 minutes to separate the mixture into two layers. The lower surfactant layer containing endotoxins was discarded to remove the endotoxins.

Further, while 10 liters of a buffer solution (TE) was supplied to the upper layer, the layer was passed through the above TFF film (Pericon 2) to replace the layer with the buffer solution. The buffer solution was then condensed to 0.5 liters.

Next, the crudely purified solution was flown through an ion exchange column and a sterile filter.

EXAMPLE 2

Pore sizes of the first TFF film 12 in FIG. 1 were studied.

Three pore sizes, i.e., 0.4 µm, 0.22 µm and 0.1 µm, of the TFF film were studied using a culture medium containing *Escherichia coli* bodies. No significant differences in film pressure, filtration efficiency and the like were observed among the three pore sizes in the concentrating and buffer solution-replacing procedures, and the culture medium could be condensed with all the three pore sizes.

In the process of removing debris after bacteriolysis, no significant differences in film pressure, filtration efficiency and the like were observed among the three pore sizes of the TFF film. For the pore size of 0.1 µm, the amount of residual proteins was less, compared with the other two sizes.

EXAMPLE 3

Pore sizes of the second TFF film 28 in FIG. 1 were studied.

Five pores sizes, i.e., 1,000 KDal, 300 KDal, 100 KDal, 50 KDal and 10 KDal, were studied. A crudely purified solution produced by the first TFF film having a pore size of 0.1 µm was condensed by filtration films having the above five pore sizes.

As a result, when it was condensed by the 1,000-KDal and 300-KDal films, plasmid DNAs were observed in filtrates, while when it was condensed by the films having a pore size of 100 KDal or smaller, no plasmid DNAs were observed. Therefore, it was confirmed that the films having a pore size of 100 KDal or smaller had better concentration efficiency.

EXAMPLE 4

Purification was performed in the same manner as in Example 1 except that the scale was changed, that is, the amount of the culture medium containing *Escherichia coli* was changed to 2 liters or 18 liters. Plasmid DNAs were purified at the same efficiency as in Example 1. Therefore, it was confirmed that the purification could be performed efficiently at different scales.

TEST EXAMPLE 1

Plasmid DNAs were purified in the same manner as in Example 1 using a beta gal plasmid vector as a test model. It was confirmed by a direct sequence method using a capillary auto-sequencer that there was no difference in base sequence between the purified plasmid DNA and the original plasmid DNA.

TEST EXAMPLE 2

Plasmid DNAS were purified in the same manner as in Example 1 using a beta gal plasmid vector as a test model. The concentration of endotoxins in the plasmid DNAs was measured by determination of absorbance using a LAL colorimetry kit (end point assay). The concentration of the endotoxins was 10 to 19 EU units.

TEST EXAMPLE 3

Plasmid DNAs were purified in the same manner as in Example 1 using a beta gal plasmid vector as a test model. This Plasmid DNAs were integrated into a mammal cell (NIH3T3) helipofectin and measured for expression efficiency. Plasmid DNAs purified by CsCl super centrifugation were used as a comparison. It was confirmed that the gene integration efficiency of the plasmid DNAs purified by the present invention was about 50% higher than that of the comparison.

The invention is based on Japanese Patent Application No. 2001-62404, which is hereby incorporated by reference.

It is to be understood by those skilled in the art that the forgoing description relates to preferred embodiments of the invention and that various changes and modifications may be made in the invention without departing from the spirit and scope thereof. Also it is to be understood that the invention is not limited to the embodiments thereof except as defined in the appended claims.

What is claimed is:

1. A vector purification device comprising
   a first TFF film with a pore size of about 2 µm or less by which a culture medium containing hosts is filtered to produce a crudely purified vector solution, and
   a second TFF film with a pore size of about 10 nm to about 4 nm by which the crudely purified vector solution is further purified.

2. A vector purification device comprising:
   a culture tank in which hosts are cultured in a culture medium,
   a TFF film by which a crudely purified vector solution obtained from the culture medium containing hosts is replaced with a buffer solution for column work, and
   an ion exchange column through which the buffer solution flows.

* * * * *